United States Patent
Hwang et al.

(10) Patent No.: US 12,187,968 B2
(45) Date of Patent: *Jan. 7, 2025

(54) METHOD FOR PREPARING SYNTHESIS GAS AND AROMATIC HYDROCARBON

(71) Applicant: LG CHEM, LTD., Seoul (KR)

(72) Inventors: Sung June Hwang, Daejeon (KR); Tae Woo Kim, Daejeon (KR); Sik Ki, Daejeon (KR); Sung Kyu Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 150 days.

This patent is subject to a terminal disclaimer.

(21) Appl. No.: 17/796,837

(22) PCT Filed: Dec. 11, 2021

(86) PCT No.: PCT/KR2021/018818
§ 371 (c)(1),
(2) Date: Aug. 1, 2022

(87) PCT Pub. No.: WO2022/270700
PCT Pub. Date: Dec. 29, 2022

(65) Prior Publication Data
US 2023/0340345 A1  Oct. 26, 2023

(30) Foreign Application Priority Data
Jun. 24, 2021 (KR) .................. 10-2021-0082421

(51) Int. Cl.
*C07C 4/02* (2006.01)
*C10J 3/62* (2006.01)

(52) U.S. Cl.
CPC .............. *C10J 3/62* (2013.01); *C07C 4/025* (2013.01); *C10J 2300/1606* (2013.01); *C10J 2300/1659* (2013.01)

(58) Field of Classification Search
CPC .................................. C07C 4/02; C10J 3/62
See application file for complete search history.

(56) References Cited

U.S. PATENT DOCUMENTS

| 3,862,899 A | 1/1975 | Murphy et al. |
| 4,938,862 A | 7/1990 | Visser et al. |

(Continued)

FOREIGN PATENT DOCUMENTS

| CN | 103087750 B | 4/2015 |
| CN | 105339470 A | 2/2016 |

(Continued)

*Primary Examiner* — Sharon Pregler
(74) *Attorney, Agent, or Firm* — Bryan Cave Leighton Paisner LLP

(57) ABSTRACT

Provided is a method for preparing synthesis gas and aromatic hydrocarbons, and more particularly, a method for preparing synthesis gas and aromatic hydrocarbons including: supplying a pyrolysis fuel oil (PFO) stream containing PFO and a pyrolysis gas oil (PGO) stream containing PGO to a distillation tower as a feed stream (S10), the PFO stream and the PGO stream being discharged from a naphtha cracking center (NCC) process; and supplying a lower discharge stream from the distillation tower to a combustion chamber for a gasification process and supplying an upper discharge stream from the distillation tower to an SM/BTX preparation process (S20).

13 Claims, 4 Drawing Sheets

(56) References Cited

U.S. PATENT DOCUMENTS

| | | |
|---|---|---|
| 2003/0083391 A1 | 5/2003 | Jahnke et al. |
| 2009/0159494 A1 | 6/2009 | Gautam et al. |
| 2010/0294994 A1 | 11/2010 | Basini et al. |
| 2018/0312767 A1 | 11/2018 | Al-Sayed et al. |
| 2019/0203130 A1* | 7/2019 | Mukherjee ............. C10G 69/10 |

FOREIGN PATENT DOCUMENTS

| | | |
|---|---|---|
| CN | 106062145 A | 10/2016 |
| CN | 110099984 A | 8/2019 |
| EP | 0916739 A2 | 5/1999 |
| EP | 3708637 A1 | 9/2020 |
| JP | 01-252696 A | 10/1989 |
| JP | 2008-50303 A | 3/2008 |
| JP | 2014-518924 A | 8/2014 |
| JP | 2020-517797 A | 6/2020 |
| KR | 10-2004-0025871 A | 3/2004 |
| KR | 10-0486162 B1 | 4/2005 |
| KR | 10-2020-0055472 A | 5/2020 |
| KR | 10-2020-0062553 A | 6/2020 |
| KR | 10-2020-0091497 A | 7/2020 |
| KR | 10-2021-0022870 A | 3/2021 |
| WO | 2016/059565 A2 | 4/2016 |
| WO | 2020/115659 A1 | 6/2020 |

* cited by examiner

[FIG. 1]
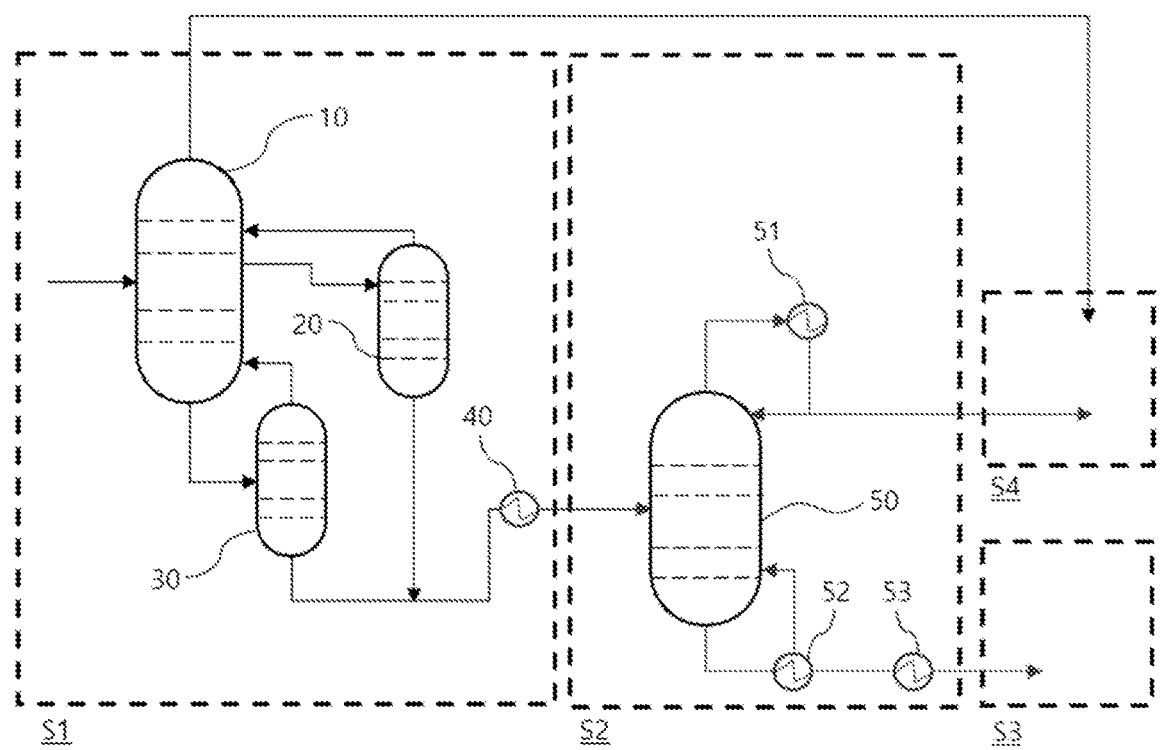

[FIG. 2]
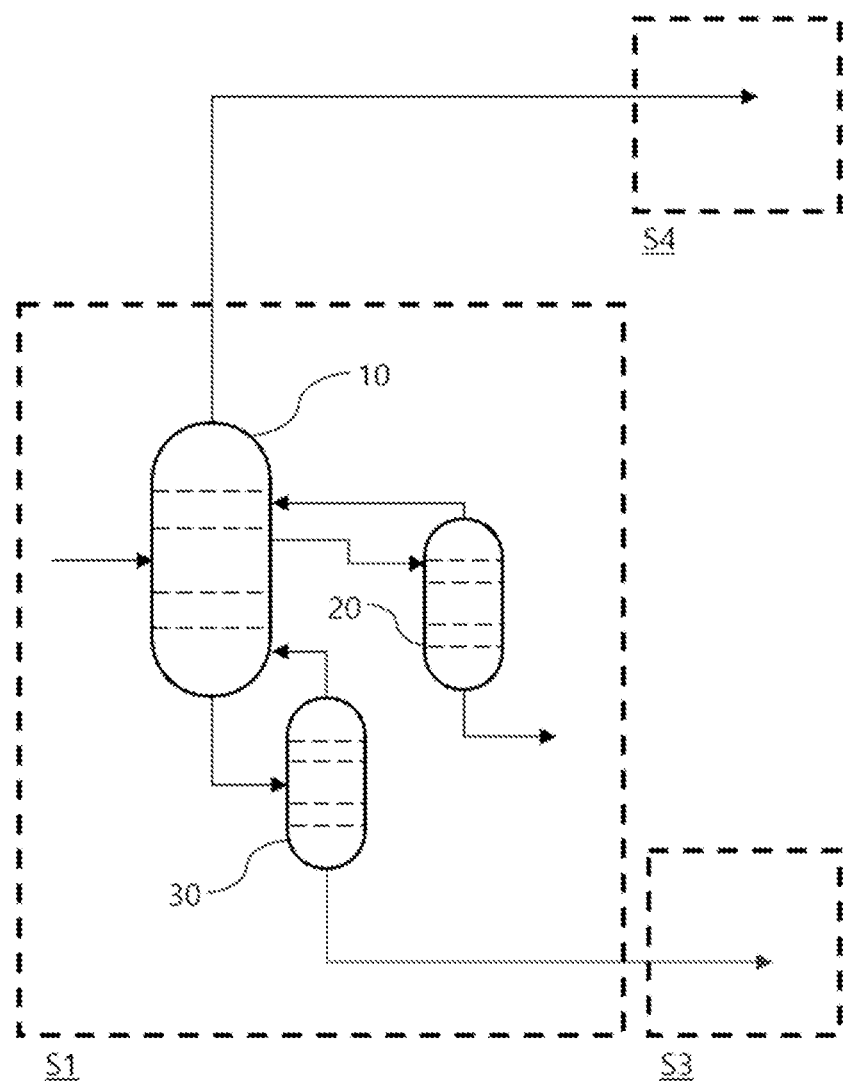

[FIG. 3]
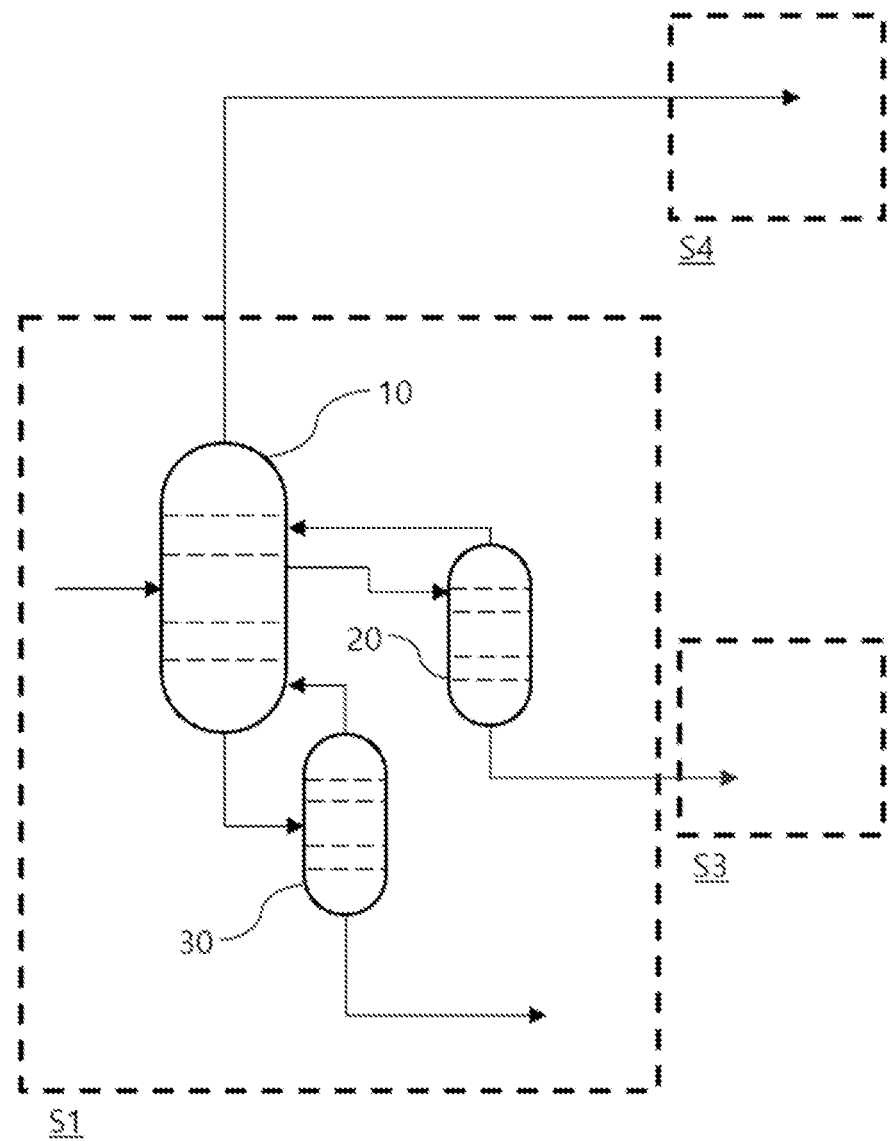

[FIG. 4]
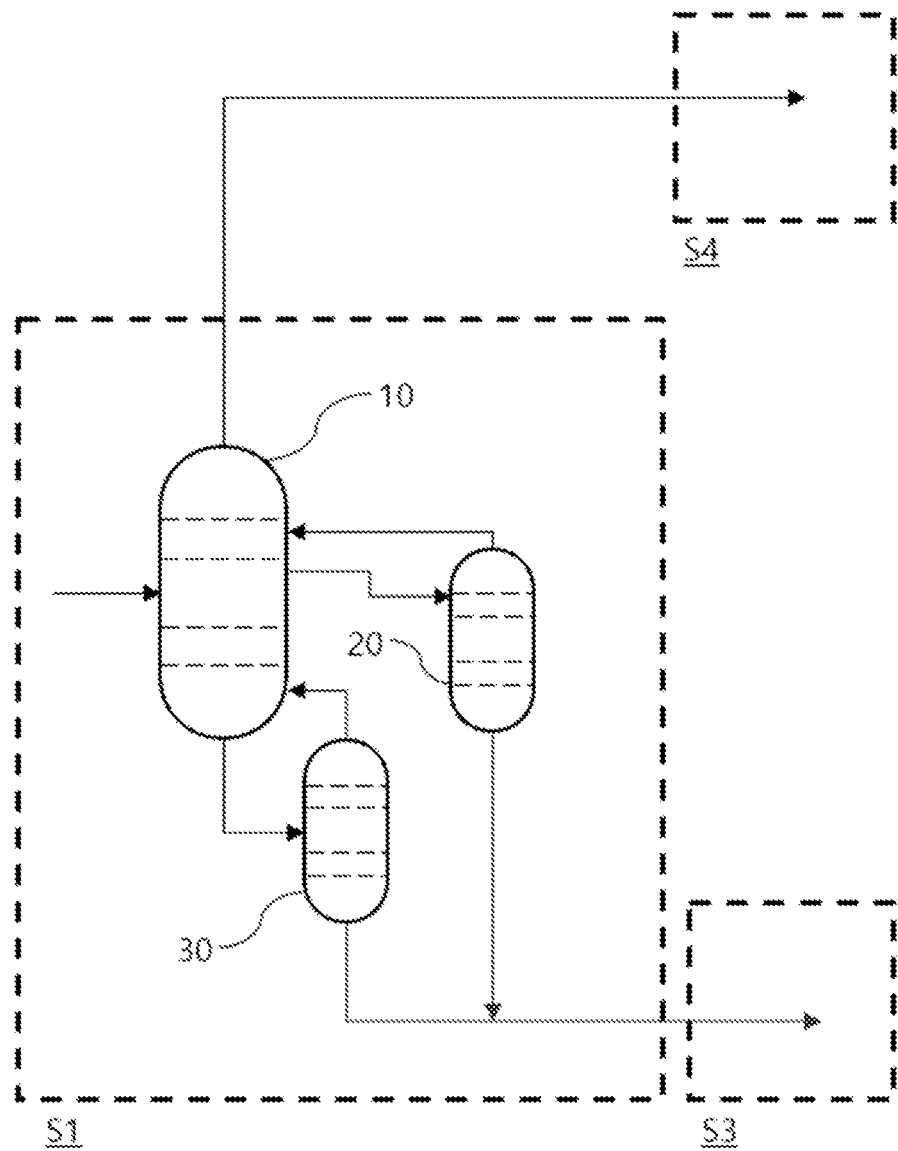

METHOD FOR PREPARING SYNTHESIS GAS AND AROMATIC HYDROCARBON

CROSS-REFERENCE TO RELATED APPLICATION

The present application is a National Phase entry pursuant to 35 U.S.C. § 371 of International Application No. PCT/KR2021/018818, filed on Dec. 11, 2021, and claims the benefit of and priority to Korean Patent Application No. 10-2021-0082421, filed on Jun. 24, 2021, the entire contents of which are incorporated by reference in their entirety for all purposes as if fully set forth herein.

TECHNICAL FIELD

The present invention relates to a method for preparing synthesis gas and aromatic hydrocarbons, and more particularly, to a method for using pyrolysis fuel oil discharged from a gasoline fractionator in a naphtha cracking center (NCC) process as a raw material for a gasification process and recovering aromatic hydrocarbons in the pyrolysis fuel oil.

BACKGROUND ART

A naphtha cracking center (hereinafter, referred to as NCC) process is a process of cracking naphtha that is a gasoline fraction at a temperature of about 950° C. to 1,050° C. to produce ethylene, propylene, butylene, and benzene, toluene, and xylene (BTX) that are basic raw materials for a petrochemical product.

In the related art, benzene, toluene, xylene, and styrene have been prepared using raw pyrolysis gasoline (RPG) that is a by-product produced in a process of producing ethylene and propylene using naphtha as a raw material, and pyrolysis fuel oil (PFO) has been used as a fuel. However, since the pyrolysis fuel oil has a high content of sulfur and a high carbon dioxide ($CO_2$) emission factor for use as a fuel without a pretreatment, the market is getting smaller due to the environmental regulations and a situation where sales are impossible in the future should be prepared for.

Meanwhile, synthesis gas (syngas) is artificially prepared gas, unlike natural gas such as naturally derived gas, methane gas, or ethane gas that is ejected from the land in oil fields and coal fields, and is prepared by a gasification process.

The gasification process is a process of converting a hydrocarbon such as coal, petroleum, or biomass as a raw material into synthesis gas mainly composed of hydrogen and carbon monoxide by pyrolysis or a chemical reaction with a gasifying agent such as oxygen, air, or water vapor. A gasifying agent and a raw material are supplied to a combustion chamber positioned at the foremost end of the gasification process to produce synthesis gas by a combustion process at a temperature of 700° C. or higher, and as a kinematic viscosity of the raw material supplied to the combustion chamber is higher, a differential pressure in the combustion chamber is increased or atomization is not smoothly performed, which causes deterioration of combustion performance or an increase in risk of explosion due to excessive oxygen.

In the related art, as a raw material for a gasification process for preparing synthesis gas using a liquid phase hydrocarbon raw material, refinery residues, such as vacuum residues (VR) and bunker-C oil, discharged from a refinery where crude oil is refined have been mainly used. However, since the refinery residue has a high kinematic viscosity, a pretreatment such as a heat treatment or addition of a diluent or water is required to use the refinery residue as the raw material for the gasification process, and since the refinery residue has high contents of sulfur and nitrogen, production of acidic gas such as hydrogen sulfide and ammonia is increased during the gasification process. Thus, in order to respond to tightened environmental regulations, a need to replace the refinery residue with a raw material having low contents of sulfur and nitrogen has been raised.

Accordingly, a method for using the pyrolysis fuel oil as a raw material for a gasification process has been considered. However, in order to use the pyrolysis fuel oil as the raw material for the gasification process, the pyrolysis fuel oil should be heated to lower a kinematic viscosity thereof, but it is difficult to satisfy a kinematic viscosity condition for use of the pyrolysis fuel oil as the raw material for the gasification process at a flash point or lower due to a significantly high kinematic viscosity of the pyrolysis fuel oil.

Therefore, the present inventors have found that when the pyrolysis fuel oil (PFO) in the naphtha cracking center (NCC) process is used as the raw material for the gasification process, greenhouse gas emissions may be reduced, operating costs of the gasification process may be reduced, and process efficiency may be improved, as compared with the case of using the refinery residue as a raw material according to the related art, thereby completing the present invention.

The background description provided herein is for the purpose of generally presenting context of the disclosure. Unless otherwise indicated herein, the materials described in this section are not prior art to the claims in this application and are not admitted to be prior art, or suggestions of the prior art, by inclusion in this section.

DISCLOSURE

Technical Problem

An object of the present invention is to provide a method for preparing synthesis gas by which greenhouse gas emissions may be reduced, operating costs of a gasification process may be reduced, and process efficiency may be improved, as compared with the case of using a refinery residue as a raw material according to the related art, by using pyrolysis fuel oil (PFO) discharged in a naphtha cracking center (NCC) process as the raw material for the gasification process.

Technical Solution

In one general aspect, a method for preparing synthesis gas and aromatic hydrocarbons includes: supplying a pyrolysis fuel oil (PFO) stream containing PFO and a pyrolysis gas oil (PGO) stream containing PGO to a distillation tower as a feed stream (S10), the PFO stream and the PGO stream being discharged in a naphtha cracking center (NCC) process; and supplying a lower discharge stream from the distillation tower to a combustion chamber for a gasification process and supplying an upper discharge stream from the distillation tower to an SM/BTX preparation process (S20).

Advantageous Effects

According to the present invention, the pyrolysis fuel oil (PFO) and the pyrolysis gas oil (PGO) in the naphtha cracking center (NCC) process are pretreated and used as the raw material for the gasification process, such that greenhouse gas emissions may be reduced, operating costs of the gasification process may be reduced, and process efficiency may be improved, as compared with the case of using the refinery residue as the raw material according to the related art.

In addition, light pyrolysis fuel oil generated during the process of pretreating the pyrolysis fuel oil (PFO) and the pyrolysis gas oil (PGO) are used as raw materials for preparing styrene and BTX together with the raw pyrolysis gasoline (RPG), such that production of aromatic hydrocarbons may be increased.

BRIEF DESCRIPTION OF DRAWINGS

FIG. 1 is a process flow diagram for a method for preparing synthesis gas and aromatic hydrocarbons according to an exemplary embodiment of the present invention.

FIG. 2 is a process flow diagram for a method for preparing synthesis gas and aromatic hydrocarbons according to Comparative Example 1 of the present invention.

FIG. 3 is a process flow diagram for a method for preparing synthesis gas and aromatic hydrocarbons according to Comparative Example 2 of the present invention.

FIG. 4 is a process flow diagram for a method for preparing synthesis gas and aromatic hydrocarbons according to Comparative Example 3 of the present invention.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention may refer to a flow of a fluid in a process, or may refer to a fluid itself flowing in a pipe. Specifically, the "stream" may refer to both a fluid itself flowing in a pipe connecting respective apparatuses to each other and a flow of a fluid. In addition, the fluid may refer to a gas or liquid, and a case in which a solid substance is included in the fluid is not excluded.

In the present invention, the term "C #" in which "#" is a positive integer represents all hydrocarbons having # carbon atoms. Therefore, the term "C8" represents a hydrocarbon compound having 8 carbon atoms. In addition, the term "C #−" represents all hydrocarbon molecules having # or fewer carbon atoms. Therefore, the term "C8−" represents a hydrocarbon compound having 8 or fewer carbon atoms. In addition, the term "C #+" represents all hydrocarbon molecules having # or more carbon atoms. Therefore, the term "C10+" represents a hydrocarbon compound having 10 or more carbon atoms.

Hereinafter, the present invention will be described in more detail with reference to FIG. 1 in order to assist in the understanding of the present invention.

According to the present invention, there is provided a method for preparing synthesis gas (syngas) and aromatic hydrocarbons. The method for preparing synthesis gas and aromatic hydrocarbons may include: supplying a pyrolysis fuel oil (PFO) stream containing PFO and a pyrolysis gas oil (PGO) stream containing PGO to a distillation tower 50 as a feed stream (S10), the PFO stream and the PGO stream being discharged in a naphtha cracking center process (S1); and supplying a lower discharge stream from the distillation tower 50 to a combustion chamber for a gasification process (S3) and supplying an upper discharge stream from the distillation tower 50 to an SM/BTX preparation process (S4) (S20).

The synthesis gas is artificially prepared gas, unlike natural gas such as naturally derived gas, methane gas, or ethane gas that is ejected from the land in oil fields and coal fields, and is prepared by the gasification process.

The gasification process is a process of converting a hydrocarbon such as coal, petroleum, or biomass as a raw material into synthesis gas mainly containing hydrogen and carbon monoxide by pyrolysis or a chemical reaction with a gasifying agent such as oxygen, air, or water vapor. Specifically, in the present invention, the synthesis gas may contain hydrogen and carbon monoxide. A gasifying agent and a raw material are supplied to a combustion chamber positioned at the foremost end of the gasification process to produce synthesis gas by a combustion process at a temperature of 700° C. or higher, and as a kinematic viscosity of the raw material supplied to the combustion chamber is higher, a differential pressure in the combustion chamber is increased or atomization is not smoothly performed, which causes deterioration of combustion performance or an increase in risk of explosion due to excessive oxygen.

In the related art, as a raw material for a gasification process for preparing synthesis gas using a liquid phase hydrocarbon raw material, refinery residues, such as vacuum residues (VR) and bunker-C oil, discharged from a refinery where crude oil is refined have been mainly used. However, since the refinery residue has a high kinematic viscosity, a pretreatment such as a heat treatment or addition of a diluent or water is required to use the refinery residue as the raw material for the gasification process, and since the refinery residue has high contents of sulfur and nitrogen, production of acidic gas such as hydrogen sulfide and ammonia is increased during the gasification process. Thus, in order to respond to tightened environmental regulations, a need to replace the refinery residue with a raw material having low contents of sulfur and nitrogen has been raised. For example, among the refinery residues, a vacuum residue may contain about 3.5 wt % of sulfur and about 3,600 ppm of nitrogen, and bunker C-oil may contain about 4.5 wt % of sulfur.

Meanwhile, pyrolysis fuel oil (PFO) discharged in a naphtha cracking center process that is a process of cracking naphtha to prepare petrochemical basic materials such as ethylene and propylene is generally used as a fuel. However, since the pyrolysis fuel oil has a high content of sulfur for use as a fuel without a pretreatment, the market is getting smaller due to the environmental regulations and a situation where sales are impossible in the future should be prepared for.

Accordingly, a method for using the pyrolysis fuel oil as a raw material for a gasification process has been considered. However, in order to use the pyrolysis fuel oil as the raw material for the gasification process, the pyrolysis fuel oil should be heated to lower a kinematic viscosity thereof, but it is difficult to satisfy a kinematic viscosity condition for use of the pyrolysis fuel oil as the raw material for the gasification process at a flash point or lower due to a significantly high kinematic viscosity of the pyrolysis fuel oil.

Accordingly, the present invention is intended to reduce greenhouse gas emissions, to reduce operating costs of a gasification process, and to improve process efficiency, as compared with the case of using a refinery residue as a raw material according to the related art, by developing a pretreatment process (S2) for using the pyrolysis fuel oil (PFO) stream containing PFO and the pyrolysis gas oil (PGO) stream containing PGO that are discharged in the naphtha cracking center process as the raw materials for the gasification process. In addition, a light PFO stream discharged in the pretreatment process (S2) is recovered to prepare styrene (SM), and benzene, toluene, and xylene (BTX), such that production of the aromatic hydrocarbons may be increased.

According to an exemplary embodiment of the present invention, the raw pyrolysis gasoline (RPG) stream containing RPG, the pyrolysis fuel oil (PFO) stream containing PFO, and the pyrolysis gas oil (PGO) stream containing PGO may be discharged in the naphtha cracking center process (S1).

Specifically, the naphtha cracking center process is a process of cracking naphtha containing paraffin, naphthene, and an aromatic compound (aromatics) to produce ethylene, propylene, butylene, and benzene, toluene, and xylene (BTX) used as petrochemical basic materials, and the naphtha cracking center process may be largely composed of a cracking process, a quenching process, a compression process, and a refining process.

The cracking process is a process of cracking naphtha into hydrocarbons having fewer carbon atoms in a cracking furnace at 800° C. or higher, and may discharge cracked gas at a high temperature. Here, the naphtha may be subjected to a preheating process with high pressure water vapor before entering the cracking furnace, and then, the preheated naphtha may be supplied to the cracking furnace.

The quenching process is a process of cooling the cracked gas at a high temperature, for suppressing a polymerization reaction of hydrocarbons in the cracked gas at a high temperature discharged from the cracking furnace, recovering waste heat, and decreasing a heat load in a subsequent process (compression process). Here, the quenching process may include primary cooling of the cracked gas at a high temperature with quench oil and secondary cooling with quench water.

Specifically, in the primary cooling, the cracked gas may be supplied to a gasoline fractionator to separate light oil containing hydrogen, methane, ethylene, propylene, and the like, the raw pyrolysis gasoline (RPG), the pyrolysis fuel oil (PFO), and the pyrolysis gas oil (PGO) from the cracked gas. Thereafter, the light oil may be transported to a subsequent compression process.

The compression process may be a process of producing compressed gas having a reduced volume by elevating a pressure of the light oil under a high pressure for economically separating and refining the light oil.

The refining process is a process of cooling the compressed gas which is compressed with a high pressure to a cryogenic temperature and then separating components in stages by a boiling point difference, and may produce hydrogen, ethylene, propylene, propane, C4 oil, raw pyrolysis gasoline (RPG), and the like.

As described above, in the quenching process in the naphtha cracking center process (S1), the raw pyrolysis gasoline (RPG), the pyrolysis fuel oil (PFO), and the pyrolysis gas oil (PGO) may be discharged. In general, the pyrolysis fuel oil (PFO) contains about 0.1 wt % or less of sulfur and about 20 ppm or less of nitrogen, and when it is used as a fuel, sulfur oxides (SOx) and nitrogen oxides (NOx) are discharged during a combustion process, and thus, environmental issues may be raised. However, in a case where the pyrolysis fuel oil (PFO) is used as a raw material of synthesis gas, the environmental issues are quite small.

Accordingly, in the present invention, the above problems may be solved by pretreating the pyrolysis fuel oil (PFO) and the pyrolysis gas oil (PGO) by the pretreatment process (S2) and using them as the raw materials for the gasification process for preparing synthesis gas, and greenhouse gas emissions may be reduced, operating costs of the gasification process may be reduced, and process efficiency may be improved, as compared with the case of using the refinery residue as the raw material for the gasification process according to the related art. In addition, a light PFO stream discharged in the pretreatment process (S2) is used as a raw material for preparing styrene and BTX, such that production of styrene and BTX may be increased.

According to an exemplary embodiment of the present invention, the PFO stream and the PGO stream of the present invention may contain pyrolysis fuel oil (PFO) and pyrolysis gas oil (PGO) discharged from a gasoline fractionator 10 in the naphtha cracking center process (S1), respectively. As a specific example, in the total number of stages of the gasoline fractionator 10, when a top stage is expressed as a stage of 1% and a bottom stage is expressed as a stage of 100%, the pyrolysis fuel oil (PFO) may be discharged at a stage of 90% or more, 95% or more, or 95% to 100%, of the total number of stages of the gasoline fractionator 10. In addition, the pyrolysis gas oil (PGO) may be discharged at a stage of 10% to 70%, 15% to 65%, or 20% to 60%, of the total number of stages of the gasoline fractionator 10. For example, when the total number of stages of the gasoline fractionator 10 is 100, a top stage may be the first stage and a bottom stage may be the 100th stage, and a stage of 90% or more of the total number of stages of the gasoline fractionator 10 may refer to the 90th stage to the 100th stage of the gasoline fractionator 10.

The PGO stream is discharged from a side portion of the gasoline fractionator 10 in the naphtha cracking center process (S1) and may be a lower discharge stream which is discharged from a lower portion of a first stripper 20 after supplying a side discharge stream containing the pyrolysis gas oil (PGO) to the first stripper 20. In addition, the PFO stream is discharged from a lower portion of the gasoline fractionator 10 in the naphtha cracking center process (S1) and may be a lower discharge stream which is discharged from a lower portion of a second stripper 30 after supplying a lower discharge stream containing the pyrolysis fuel oil (PFO) to the second stripper 30.

The first stripper 20 and the second stripper 30 may be devices in which a stripping process of separating and removing gas or vapor dissolved in a liquid is performed, and may be performed by methods such as direct contact, heating, and pressurization by, for example, steam, inert gas, or the like. As a specific example, the side discharge stream from the gasoline fractionator 10 is supplied to the first stripper 20, such that an upper discharge stream containing a light fraction separated from the side discharge stream from the gasoline fractionator 10 may be refluxed from the first stripper 20 to the gasoline fractionator 10. In addition, the lower discharge stream from the gasoline fractionator 10 is supplied to the second stripper 30, such that an upper discharge stream containing a light fraction separated from the lower discharge stream from the gasoline fractionator 10 may be refluxed from the second stripper 30 to the gasoline fractionator 10.

According to an exemplary embodiment of the present invention, the PGO stream may contain 70 wt % or more or 70 wt % to 95 wt % of C10 to C12 hydrocarbons, and the PFO stream may contain 70 wt % or more or 70 wt % to 98 wt % of C13+ hydrocarbons. For example, the PGO stream containing 70 wt % or more of C10 to C12 hydrocarbons may have a kinematic viscosity at 40° C. of 1 to 200 cSt and a flash point of 10 to 50° C. In addition, for example, the PFO stream containing 70 wt % or more of C13+ hydrocarbons may have a kinematic viscosity at 40° C. of 400 to 100,000 cSt and a flash point of 70 to 200° C. As such, the PFO stream containing more heavy hydrocarbons than the PGO stream may have a higher kinematic viscosity and a higher flash point than the pyrolysis gas oil under the same temperature conditions.

According to an exemplary embodiment of the present invention, a boiling point of the PGO stream may be 200 to 288° C. or 210 to 270° C., and a boiling point of the PFO stream may be 289° C. to 550° C. or 300 to 500° C.

The boiling points of the PGO stream and the PFO stream may refer to boiling points of a PGO stream and a PFO stream in a bulk form, each composed of a plurality of hydrocarbons. Here, the types of hydrocarbons contained in the PGO stream and the types of hydrocarbons contained in the PFO stream may be different from each other, and some types may be the same as each other. As a specific example, the types of hydrocarbons contained in the PGO stream and the PFO stream may be included as described above.

According to an exemplary embodiment of the present invention, the raw pyrolysis gasoline (RPG) stream containing RPG discharged from the gasoline fractionator 10 in the naphtha cracking center process (S1) may be supplied to the SM/BTX preparation process (S4) to prepare styrene and BTX. The BTX is an abbreviation of benzene, toluene, and xylene, and the xylene may include ethyl benzene, m-xylene, o-xylene, and p-xylene.

As a specific example, the RPG stream may be a stream containing raw pyrolysis gasoline (RPG) discharged at a stage of 5% or less or 1% to 5%, of the total number of stages of the gasoline fractionator 10. Specifically, the RPG stream containing raw pyrolysis gasoline (RPG) discharged from the gasoline fractionator 10 is discharged from an upper portion of the gasoline fractionator 10, and may be a stream separated by supplying an upper discharge stream containing the raw pyrolysis gasoline (RPG) to an NCC subsequent process (not illustrated) and removing hydrogen and C4− hydrogen substances.

A plurality of RPG streams are discharged at various stages of the NCC subsequent process while the upper discharge stream from the gasoline fractionator 10 is subjected to a separation procedure in the NCC subsequent process (not illustrated), and the plurality of RPG streams may be supplied at different positions in the SM/BTX preparation process (S4) according to components. For example, the RPG stream may be discharged from a lower portion of a gasoline striper (not illustrated) in the NCC subsequent process (not illustrated), and may include an RPG stream containing styrene and an RPG stream discharged from a lower portion of a C4 separation column (not illustrated) in the NCC subsequent process (not illustrated) and containing no styrene.

The RPG stream containing styrene may be a C5+ hydrocarbon mixture, and specifically, may be a mixture in which C5 hydrocarbons to C10 hydrocarbons are rich. For example, the RPG stream containing styrene may include one or more selected from the group consisting of isopentane, n-pentane, 1,4-pentadiene, dimethylacetylene, 1-pentene, 3-methyl-1-butene, 2-methyl-1-butene, 2-methyl-2-butene, isoprene, trans-2-pentene, cis-2-pentene, trans-1,3-pentadiene, cyclopentadiene, cyclopentane, cyclopentene, n-hexane, cyclohexane, 1,3-cyclohexadiene, n-heptane, 2-methylhexane, 3-methylhexane, n-octane, n-nonane, benzene, toluene, ethylbezene, m-xylene, o-xylene, p-xylene, styrene, dicyclopentadiene, and indane. Here, a content of C6 to C8 hydrocarbons in the RPG stream may be 40 wt % or more, 45 wt % to 75 wt %, or 50 wt % to 70 wt %. In this case, the RPG stream containing styrene may be supplied to an SM process unit in the SM/BTX preparation process (S4). Specifically, the RPG stream containing styrene may be supplied to the SM process unit to separate styrene, and the residual stream from which styrene is separated in the SM process unit may be supplied to a BTX process unit to separate benzene, toluene, and xylene.

In addition, the stream containing no styrene may include, for example, one or more selected from the group consisting of cyclopentadiene, pentadiene, isoprene, cyclopentene, 1-pentene, 3-methyl-1-butene, cyclopentane, 2-methyl-butene, n-pentane, benzene, toluene, and C6 non-aromatic hydrocarbons. In this case, the RPG stream containing no styrene may be supplied to the BTX process unit in the SM/BTX preparation process (S4). Specifically, the RPG stream containing no styrene is supplied to the BTX process unit in the SM/BTX preparation process (S4) without passing through the SM process unit, such that energy may be saved because unnecessary process steps such as separation and mixing required when supplied to the SM process unit in the SM/BTX preparation process (S4) are not performed.

According to an exemplary embodiment of the present invention, the PFO stream containing pyrolysis fuel oil (PFO) and the PGO stream containing pyrolysis gas oil (PGO) may be supplied to the distillation tower 50 as a feed stream, the PFO stream and the PGO stream being discharged in the naphtha cracking center process (S1).

The feed stream supplied to the distillation tower 50 includes both the PGO stream and the PFO stream, and may contain both heavy oil (heavies) and light oil (lights). As such, the feed stream containing both the heavy oil and light oil is supplied to the distillation tower 50, and the upper discharge stream containing a light PFO stream is discharged from an upper portion of the distillation tower 50, such that a lower discharge stream having an adjusted kinematic viscosity and flash point may be discharged from a lower portion of the distillation tower 50. As a specific example, the PFO stream having a higher content of heavy oil than the PGO stream may have a higher kinematic viscosity and a higher flash point than the PGO stream, and the PGO stream having a higher content of light oil than the PFO stream may have a lower kinematic viscosity and a lower flash point than the PFO stream. In the feed stream including both two conflicting streams, a stream having a desired kinematic viscosity and flash point may be discharged from the lower portion of the distillation tower 50 by removing the light oil, as described above.

According to an exemplary embodiment of the present invention, the feed stream may be a mixed oil stream obtained by mixing the PFO stream and the PGO stream. In this case, for example, a ratio of a flow rate of the mixed oil stream to a flow rate of the PGO stream contained in the mixed oil stream (hereinafter, referred to as a "flow rate ratio of the PGO stream") may be 0.35 to 0.7, 0.4 to 0.65, or 0.4 to 0.6, but is not limited thereto. Here, the "flow rate" may refer to a flow of a weight per unit hour. As a specific example, a unit of the flow rate may be kg/h.

A boiling point of the mixed oil stream may be 200° C. to 600° C., 210 to 550° C., or 240° C. to 500° C. The boiling point of the mixed oil stream may refer to a boiling point of a mixed oil stream in a bulk form composed of a plurality of hydrocarbons.

According to an exemplary embodiment of the present invention, the mixed oil stream may pass through a first heat exchanger 40 before being supplied to the distillation tower 50, and then may be supplied to the distillation tower 50. The mixed oil stream is produced by mixing the PGO stream and the PFO stream at a high temperature discharged from the first stripper 20 or the second stripper 30, and the temperature of the mixed oil stream at the time of supply to the distillation tower 50 may be optimally adjusted and also process energy may be reduced by reusing the sensible heat of the mixed oil stream in the process, if necessary.

According to an exemplary embodiment of the present invention, the mixed oil stream may be supplied to a stage of 10% to 70%, 15% to 60%, or 20% to 50%, of the total number of stages of the distillation tower 50. Within this range, the distillation tower 50 may be efficiently operated, and unnecessary energy consumption may be significantly reduced.

According to an exemplary embodiment of the present invention, a ratio of a flow rate of the feed stream supplied to the distillation tower 50 to a flow rate of the upper discharge stream from the distillation tower 50 (hereinafter, referred to as a "distillation ratio of the distillation tower 50") may be 0.01 to 0.2, 0.01 to 0.15, or 0.03 to 0.15. That is, the distillation ratio of the distillation tower 50 may be adjusted to 0.01 to 0.2, 0.01 to 0.15, 0.03 to 0.15, or 0.1 to 0.2.

The distillation ratio of the distillation tower 50 in the above range may be adjusted by a flow rate adjustment device (not illustrated) installed in a pipe through which the upper discharge stream from the distillation tower 50 is transported, and the performance of the distillation tower 50 may be performed by adjusting a reflux ratio of the upper discharge stream from the distillation tower 50 using the distillation ratio and a second heat exchanger 51. Here, the reflux ratio may refer to a ratio of a flow rate of a reflux stream to a flow rate of an outflow stream, and as a specific example, the reflux ratio of the upper discharge stream from the distillation tower 50 may refer to, when a part of the upper discharge stream from the distillation tower 50 is branched and refluxed to the distillation tower 50 as a reflux stream and the rest is supplied to the SM/BTX preparation process (S4) as an outflow stream, a ratio of a flow rate of the reflux stream to a flow rate of the outflow stream (hereinafter, referred to as a "reflux ratio"). As a more specific example, the reflux ratio may be 0.01 to 10, 0.1 to 7, or 0.15 to 5.

A gasifying agent and a raw material may be supplied to the combustion chamber (not illustrated) positioned at the foremost end of the gasification process (S3) to produce synthesis gas by a combustion process at a temperature of 700° C. or higher. Here, the reaction of producing synthesis gas is performed under a high pressure of 20 to 80 atm, and the raw material in the combustion chamber should be moved at a high flow velocity of 2 to 40 m/s. Therefore, the raw material should be pumped at a high flow velocity under a high pressure for the reaction of producing synthesis gas, and when a kinematic viscosity of the raw material supplied to the combustion chamber is higher than an appropriate range, a high-priced pump should be used due to reduced pumpability or costs are increased due to increased energy consumption, and pumping may be impossible under desired conditions. In addition, since pumping is not smoothly performed, the raw material may not be uniformly supplied to the combustion chamber. In addition, since a differential pressure in the combustion chamber is raised or uniform atomization of the raw material is not smoothly performed due to its small particle size, combustion performance may be deteriorated, productivity may be lowered, a large amount of the gasifying agent may be required, and a risk of explosion may be increased due to excessive oxygen. Here, an appropriate range of the kinematic viscosity may be somewhat different depending on the type of synthesis gas to be synthesized, conditions of the combustion process performed in the combustion chamber, and the like. However, in general, a lower kinematic viscosity of the raw material is better in terms of costs, productivity, and safety, at a temperature of the raw material at the time of supply to the combustion chamber in the gasification process (S3). The kinematic viscosity may be preferably in a range of 300 cSt or less. A differential pressure rise in the combustion chamber is prevented within the range, and atomization is smoothly performed, such that combustion performance may be improved and reactivity may be improved due to smooth combustion reaction.

In addition, when a flash point of the raw material supplied to the combustion chamber is lower than an appropriate range, a flame may occur in a burner before combustion reaction occurrence due to the low flash point, a risk of explosion may occur due to a backfire phenomenon of the flame in the combustion chamber, and the refractories in the combustion chamber may be damaged. Here, an appropriate range of the flash point may vary depending on the type of synthesis gas to be synthesized in the combustion chamber, conditions of the combustion process performed in the combustion chamber, and the like. However, in general, the flash point of the raw material may be preferably in a range of being higher than the temperature of the raw material at the time of supply to the combustion chamber in the gasification process (S3) by 25° C. or more, and within the range, a loss of the raw material, an explosion risk, and damage of refractories in the combustion chamber may be prevented.

Accordingly, in the present invention, in order to control the kinematic viscosity and the flash point of the lower discharge stream from the distillation tower 50 that is the raw material supplied to the combustion chamber in the gasification process (S3) to appropriate ranges, the distillation ratio of the distillation tower 50 may be adjusted. That is, by adjusting the distillation ratio of the distillation tower 50, the kinematic viscosity and the flash point of the lower discharge stream from the distillation tower 50 may be controlled to appropriate ranges, at a temperature when the lower discharge stream from the distillation tower 50 is supplied to the combustion chamber. In addition, by adjusting the distillation ratio of the distillation tower 50, the composition in the upper discharge stream from the distillation tower 50 is controlled, and when the upper discharge stream from the distillation tower 50 is supplied to the SM/BTX preparation process (S4), production of styrene and BTX may be increased.

According to an exemplary embodiment of the present invention, a third heat exchanger 52 may be operated as a general reboiler.

According to an exemplary embodiment of the present invention, the temperature of the lower discharge stream from the distillation tower 50 at the time of supply to the combustion chamber may be lower than the flash point of the lower discharge stream from the distillation tower 50 at the time of supply to the combustion chamber by 25° C. or more, and may be a temperature having a kinematic viscosity of 300 cSt or less. That is, the kinematic viscosity of the lower discharge stream of the distillation tower 50 at the time of supply to the combustion chamber may be 300 cSt or less or 1 cSt to 300 cSt, and the flash point of the lower discharge stream of the distillation tower 50 may be higher than the temperature at the time of supply to the combustion chamber by 25° C. or more or 25° C. to 150° C. Here, the temperature of the lower discharge stream of the distillation tower 50 at the time of supply to the combustion chamber may be 20° C. to 90° C. or 30° C. to 80° C. The kinematic viscosity of the lower discharge stream from the distillation tower 50 at the temperature at the time of supply to the combustion chamber within the range may be 300 cSt or less and the temperature at the time of supply to the combustion chamber may be further lower than the flash point by 25° C. or more, and thus, may satisfy the process operating conditions for use as the raw material for the gasification process (S3).

Specifically, by adjusting the distillation ratio of the distillation tower 50 to 0.01 to 0.2, 0.01 to 0.15, or 0.03 to 0.15, when the lower discharge stream from the distillation tower 50 is supplied to the combustion chamber, the flash point of the lower discharge stream from the distillation tower 50 may be higher than the temperature of the lower discharge stream from the distillation tower 50 at the time of supply by 25° C. or more, and the kinematic viscosity thereof may be in a range of 300 cSt or less at the temperature of the lower discharge stream from the distillation tower 50 at the time of supply.

When the distillation ratio of the distillation tower 50 is 0.01 to 0.2, a light material having a low flash point is removed in the situation where both the flash point and the kinematic viscosity are low, such that an increase range of the flash point is more increased than an increase range of the kinematic viscosity. Therefore, the flash point and the kinematic viscosity when the lower discharge stream from the distillation tower 50 is supplied to the combustion chamber may be controlled to the ranges of the flash point and the kinematic viscosity described above. On the other hand, when the distillation ratio of the distillation tower 50 is less than 0.01, it is difficult to control the flash point when the lower discharge stream from the distillation tower 50 is supplied to the combustion chamber to be higher than the temperature when the lower discharge stream from the distillation tower 50 is supplied to the combustion chamber by 25° C. or more, and when the distillation ratio of the distillation tower 50 is more than 0.2, the increase range of the kinematic viscosity is more increased than the increase range of the flash point, and thus, it is difficult to control the kinematic viscosity to 300 cSt or less.

As such, by adjusting the distillation ratio of the distillation tower 50, the flash point and the kinematic viscosity of the lower discharge stream from the distillation tower 50 at the time of supply to the combustion chamber may be controlled, and thus, the lower discharge stream from the distillation tower may have physical properties appropriate for use as the raw material for the gasification process (S3).

Meanwhile, for example, when the PFO stream is directly supplied to the combustion chamber without the pretreatment process (S2) as illustrated in FIG. 2, the PGO stream is directly supplied to the combustion chamber without the pretreatment process (S2) as illustrated in FIG. 3, or the mixed oil stream of the PGO stream and the PFO stream is directly supplied to the combustion chamber without the pretreatment process (S2) according to the present invention as illustrated in FIG. 4, a temperature satisfying both the kinematic viscosity and the flash point in the appropriate ranges described above may not exist. As such, when the PFO stream, the PGO stream, or the mixed oil stream is supplied to the combustion chamber at the temperature which does not satisfy any one of the kinematic viscosity and the flash point in the appropriate ranges, a differential pressure in the combustion chamber may be raised or atomization may not be smoothly performed to deteriorate combustion performance, and an explosion risk may be increased due to excessive oxygen, or a flame may occur in the burner before combustion reaction occurrence, and an explosion risk may be present due to a backfire phenomenon of the flame in the combustion chamber and refractories in the combustion chamber may be damaged.

In general, the PFO stream and the PGO stream are the heaviest residues in the NCC process and have been used as a simple fuel, and when they are used as a simple fuel as such, it is not necessary to adjust the compositions and the physical properties thereof. However, as in the present invention, in order to use the stream as the raw material of the synthesis gas, specific physical properties, for example, both a kinematic viscosity and a flash point should be satisfied. However, the PGO stream satisfies the kinematic viscosity but has a flash point that is too low, and the PFO stream has a high flash point but has a kinematic viscosity that is too high, and thus, each stream may not satisfy both the kinematic viscosity and the flash point and it is difficult to use each of the streams as the raw material of the synthesis gas. In addition, in a case where the entire stream of the PFO stream and the PGO stream is used as the raw material of the synthesis gas, a ratio of the flow rate of the PGO stream to a flow rate of the entire stream of the PFO stream and the PGO stream is generally about 0.35 to 0.7, and in this case also, the kinematic viscosity condition for use as the raw material for the gasification process at the flash point or lower may not be satisfied and it is difficult to use the stream as the raw material of the synthesis gas. In this regard, in the present invention, the entire amount of the PFO stream and the PGO stream is supplied to the distillation tower 50 and pretreated, such that when the lower discharge stream from the distillation tower 50 is supplied to the combustion chamber, the flash point of the lower discharge stream from the distillation tower 50 may be controlled to a range higher than the temperature of the lower discharge stream from the distillation tower 50 at the time of supply by 25° C. or more, and the kinematic viscosity may also be controlled to a range of 300 cSt or less at the temperature of the lower discharge stream from the distillation tower 50 at the time of supply, and thus, the conditions for use the stream as the raw material of the synthesis gas may be satisfied.

According to an exemplary embodiment of the present invention, the lower discharge stream from the distillation tower 50 may pass through a fourth heat exchanger 53 before being supplied to the gasification process (S3), and then may be supplied to the gasification process (S3). In this case, the temperature of the lower discharge stream from the distillation tower 50 at the time of supply to gasification process (S3) may be adjusted and also process energy may be reduced by reusing the sensible heat of the lower discharge stream from the distillation tower 50 which may be wasted as waste heat in the process using the heat exchanger.

According to an exemplary embodiment of the present invention, the upper discharge stream from the distillation tower 50 may be supplied to the SM/BTX preparation process (S4) to prepare aromatic hydrocarbons containing styrene.

According to an exemplary embodiment of the present invention, the lower discharge stream from the distillation tower 50 may have a content of C10+ hydrocarbons of 80 wt % or more or 80 wt % to 98 wt % and a content of C8-hydrocarbons of 5 wt % or less or 0.01 wt % to 5 wt %, and the upper discharge stream from the distillation tower 50 may have a content of C6 to C8 aromatic hydrocarbons of 50 wt % or more, 55 wt % to 95 wt %, or 55 wt % to 85 wt % and a content of styrene of 20 wt % to 50 wt %, 20 wt % to 45 wt %, or 25 wt % to 45 wt %.

For example, the C8− hydrocarbon may include one or more selected from the group consisting of pentane, pentene, pentadiene, methylbutene, cyclopentane, cyclopentene, hexane, cyclohexane, heptane, methylhexane, octane, benzene, toluene, xylene, and styrene. As a specific example, the C8− hydrocarbon may include all types of C8− hydrocarbons described above, but the present invention is not limited thereto.

In addition, for example, the C10+ hydrocarbon may include one or more selected from the group consisting of dicyclopentadiene, naphthalene, methylnaphthalene, tetramethylbenzene, fluorene, and anthracene. As a specific example, the C10+ hydrocarbon may include all types of C10+ hydrocarbons described above, but the present invention is not limited thereto.

In addition, for example, the C6 to C8 aromatic hydrocarbons may include one or more selected from the group consisting of benzene, toluene, xylene, and styrene, and the C8 aromatic hydrocarbon may include styrene. As a specific example, the C6 to C8 aromatic hydrocarbons may include all types of C6 to C8 aromatic hydrocarbons described above, but the present invention is not limited thereto.

As such, the lower discharge stream from the distillation tower 50 is used as the raw material of synthesis gas, and the upper discharge stream from the distillation tower 50 in which the content of the C6 to C8 aromatic hydrocarbons is 50 wt % or more and the content of the styrene is 20 wt % to 50 wt % is supplied to the SM/BTX preparation process (S4), such that the pyrolysis fuel oil may be used as the raw material for the gasification process, and the aromatic hydrocarbons in the pyrolysis fuel oil may be recovered to increase production of aromatic hydrocarbons containing styrene.

According to an exemplary embodiment of the present invention, burning the lower discharge stream from the distillation tower 50 supplied to the combustion chamber in the gasification process (S3) at a temperature of 700° C. or higher, 700° C. to 2,000° C., or 800° C. to 1,800° C. may be further included. In addition, the lower discharge stream from the distillation tower 50 may be supplied to the combustion chamber together with the gasifying agent. Here, the gasifying agent may include one or more selected from the group consisting of oxygen, air, and water vapor, and as a specific example, the gasifying agent may be oxygen or water vapor.

As such, the lower discharge stream from the distillation tower 50 is burned at a high temperature in the presence of the gasifying agent, such that the synthesis gas may be prepared. The synthesis gas prepared according to the preparation method of the present invention contains carbon monoxide and hydrogen and may further contain one or more selected from the group consisting of carbon dioxide, ammonia, hydrogen sulfide, hydrogen cyanide, and carbonyl sulfide.

According to an exemplary embodiment of the present invention, the SM/BTX preparation process (S4) is a process of preparing styrene and BTX by receiving the RPG stream and the upper discharge stream from the distillation tower 50, and may include an SM process unit and a BTX process unit. Here, the SM process unit may be positioned in front of the BTX process unit.

According to an exemplary embodiment of the present invention, the RPG stream containing styrene among the RPG streams and the upper discharge stream from the distillation tower 50 may be supplied to the SM process unit in the SM/BTX preparation process (S4) to prepare styrene. Here, the RPG stream containing styrene and the upper discharge stream from the distillation tower 50 may be supplied to the SM process unit in the SM/BTX preparation process (S4) as a separate stream or a mixed stream.

The RPG stream containing styrene and the upper discharge stream from the distillation tower 50 may be supplied to a C7 separation column of the SM process unit. In the C7 separation column of the SM process unit, the stream may be separated into an upper discharge stream containing C7− hydrocarbons and a lower discharge stream containing C8+ hydrocarbons.

The lower discharge stream containing C8+ hydrocarbons may be supplied to a C8 separation column of the SM process unit. In the C8 separation column of the SM process unit, the stream may be separated into an upper discharge stream containing C8 hydrocarbons and a lower discharge stream containing C9+ hydrocarbons.

The upper discharge stream discharged from the C8 separation column of the SM process unit may be supplied to an extractive distillation column of the SM process unit, and other hydrocarbons containing styrene and xylene contained in the upper discharge stream from the C8 separation column of the SM process unit may be separated using an extraction solvent in the extractive distillation column of the SM process unit. Specifically, in the extractive distillation column of the SM process unit, the styrene contained in the upper discharge stream from the C8 separation column may be selectively extracted and separated as a lower discharge stream, and the other hydrocarbons may be separated as an upper discharge stream. Here, the lower discharge stream from the extractive distillation column of the SM process unit may be supplied to a solvent recovery column to remove the extraction solvent, and then the styrene may be separated.

A residual stream discharged from the SM process unit may be supplied to the BTX process unit. Specifically, the upper discharge stream from the C7 separation column, the lower discharge stream from the C8 separation column, and the upper discharge stream from the extractive distillation column of the SM process unit may be mixed and supplied to a hydrodesulfurization unit of the BTX process unit as a residual stream. In addition, benzene, toluene, and xylene may be prepared using the residual stream from the SM process unit supplied to the BTX process unit.

According to an exemplary embodiment of the present invention, the RPG stream containing no styrene among the RPG streams and the residual stream from the SM process unit may be supplied to the BTX process unit to prepare benzene or BTX.

According to an exemplary embodiment of the present invention, the RPG stream containing no styrene and the residual stream from the SM process unit may be supplied to the hydrodesulfurization unit of the BTX process unit to cause hydrodesulfurization in the presence of separately supplied hydrogen and a catalyst. The catalyst may be a catalyst capable of selective hydrogenation. For example, the catalyst may include one or more selected from the group consisting of palladium, platinum, copper, and nickel. In some cases, the catalyst may be used by being supported on one or more carriers selected from the group consisting of gamma alumina, activated carbon, and zeolite.

A discharge stream from the hydrodesulfurization unit of the BTX process unit may be supplied to a C5 separation column of the BTX process unit. An upper discharge stream containing C5– aromatic hydrocarbons may be discharged from the C5 separation column, and a lower discharge stream containing C6+ aromatic hydrocarbons may be supplied to a C7 separation column.

An upper discharge stream containing C7– aromatic hydrocarbons may be supplied from the C7 separation column of the BTX process unit to an extractive distillation column of the BTX process unit, and a lower discharge stream containing C8+ aromatic hydrocarbons may be supplied to a xylene separation column of the BTX process unit.

In the extractive distillation column of the BTX process unit, aromatic hydrocarbons and non-aromatic hydrocarbons contained in the upper discharge stream from the C7 separation column may be separated using an extraction solvent. Specifically, in the extractive distillation column of the BTX process unit, the aromatic hydrocarbons contained in the upper discharge stream from the C7 separation column of the BTX process unit may be selectively extracted and separated as a lower discharge stream, and the non-aromatic hydrocarbons may be separated as an upper discharge stream. For example, the extraction solvent may include one or more selected from the group consisting of sulfolane, alkyl-sulfolane, N-formylmorpholine, N-methylpyrrolidone, tetraethylene glycol, triethylene glycol, and diethylene glycol. In addition, the extraction solvent may further include water as a co-solvent.

The lower discharge stream from the extractive distillation column of the BTX process unit contains C7– aromatic hydrocarbons, and may be supplied to a benzene separation column of the BTX process unit to separate benzene from an upper discharge stream from the benzene separation column of the BTX process unit, and a lower discharge stream from the benzene separation column may be supplied to a toluene separation column of the BTX process unit. Here, the lower discharge stream from the extractive distillation column supplied to the benzene separation column of the BTX process unit may pass through a solvent recovery column for removing the extraction solvent, and then may be supplied to the benzene separation column.

The lower discharge stream from the benzene separation column of the BTX process unit contains C7 aromatic hydrocarbons, and may be supplied to the toluene separation column of the BTX process unit to separate toluene from an upper discharge stream from the toluene separation column, and a lower discharge stream from the toluene separation column may be supplied to a xylene separation column of the BTX process unit.

The lower discharge stream from the C7 separation column of the BTX process unit and the lower discharge stream from the toluene separation column of the BTX process unit may be supplied to the xylene separation column of the BTX process unit to separate xylene from an upper discharge stream, and the rest C9+ hydrocarbon heavy substances may be discharged from a bottom portion.

According to an exemplary embodiment of the present invention, in the method for preparing synthesis gas and aromatic hydrocarbons, if necessary, devices such as a valve, a pump, a separator, and a mixer may be further installed.

Hereinabove, the method for preparing synthesis gas and aromatic hydrocarbons according to the present invention has been described and illustrated in the drawings, but the description and the illustration in the drawings are the description and the illustration of only core constitutions for understanding of the present invention, and in addition to the process and devices described above and illustrated in the drawings, the process and the devices which are not described and illustrated separately may be appropriately applied and used for carrying out the method for preparing synthesis gas and aromatic hydrocarbons according to the present invention.

Hereinafter, the present invention will be described in more detail by Examples. However, the following Examples are provided for illustrating the present invention. It is apparent to those skilled in the art that various modifications and alterations may be made without departing from the scope and spirit of the present invention, and the scope of the present invention is not limited thereto.

EXAMPLES

Examples 1 to 5

According to the process flow diagram illustrated in FIG. 1, synthesis gas, styrene, and BTX were prepared.

Specifically, an upper discharge stream discharged at a stage of 1% of the total number of stages of a gasoline fractionator 10 in a naphtha cracking center process (S1) was supplied to an NCC subsequent process (not illustrated), and an RPG stream containing styrene and an RPG stream containing no styrene were discharged in the NCC subsequent process. In addition, a side discharge stream discharged at a stage of 40% of the total number of stages of the gasoline fractionator 10 was supplied to a first stripper 20, and then a pyrolysis gas oil (PGO) stream containing PGO was discharged from a lower portion of the first stripper 20, and at this time, it was confirmed that a content of C10 to C12 hydrocarbons in the PGO stream was 86 wt %. In addition, a lower discharge stream discharged at a stage of 100% of the total number of stages of the gasoline fractionator 10 was supplied to a second stripper 30, and then a pyrolysis fuel oil (PFO) stream containing PFO was discharged from a lower portion of the second stripper 30, and at this time, it was confirmed that a content of C13+ hydrocarbons in the PFO stream was 89 wt %. In addition, the PGO stream had a flash point of 25.5° C. and a kinematic viscosity at 40° C. of 75 cSt, and the PFO stream had a flash point of 98° C. and a kinematic viscosity at 40° C. of 660 cSt.

A mixed oil stream obtained by mixing the PGO stream and the PFO stream was supplied to a distillation tower 50, and then, a distillation ratio of the distillation tower 50 was adjusted and an upper discharge stream from the distillation tower 50 was discharged, and a lower discharge stream from the distillation tower 50 was supplied to a combustion chamber in a gasification process (S3) together with oxygen and vapor, thereby preparing synthesis gas containing hydrogen and carbon monoxide. At this time, a ratio of a flow rate of the PGO stream to a flow rate of the mixed oil stream was 0.42, and the mixed oil stream had a flash point of 70° C. and a kinematic viscosity at 40° C. of 365 cSt. In addition, a reflux ratio of the mixed oil stream from the distillation tower 50 was adjusted to 2.5.

The RPG stream containing styrene and the upper discharge stream from the distillation tower 50 were supplied to an SM process unit in an SM/BTX preparation process (S4) to prepare styrene using a C7 separation column, a C8 separation column, and an extractive distillation column, and a residual stream from the SM process unit was supplied to a BTX process unit.

The RPG stream containing no styrene and the residual stream from the SM process unit were supplied to the BTX process unit in the SM/BTX preparation process (S4) to prepare benzene, toluene, and xylene using a hydrodesulfurization unit, a C5 separation column, a C7 separation column, an extractive distillation column, a benzene separation column, a toluene separation column, and a xylene separation column.

The content ratios of the C6 to C8 aromatic hydrocarbons in the lower discharge stream and the upper discharge stream from the distillation tower 50, the distillation ratio of the distillation tower 50, and the temperature and the flash point of the lower discharge stream from the distillation tower 50 at the time of supply to the combustion chamber were measured. The results are shown in Table 1. In addition, it was confirmed whether the process operating standards were satisfied according to the measurement results. At this time, the time when the lower discharge stream from the distillation tower 50 was supplied to the combustion chamber was set to temperature conditions to control the kinematic viscosity to 300 cSt using a fourth heat exchanger 53. Specifically, in order to derive the temperature conditions to control the kinematic viscosity to 300 cSt, the kinematic viscosity of the corresponding sample was measured by temperature, and then, a correlation between the temperature and the viscosity was established and calculated using interpolation.

In addition, the production of styrene, benzene, toluene, and xylene produced in the SM/BTX preparation process (S4) is shown in Table 3.

The kinematic viscosity and the flash point were measured as follows, and were applied to all of Examples and Comparative Examples.
  (1) Kinematic viscosity: A sample was obtained from the stream of the sample to be measured and measurement was performed based on ASTM D7042 using SVM 3001 available from Anton Paar. In addition, the temperature of each of the samples was maintained at a temperature lower than a kinematic viscosity measurement temperature by 10° C., and the sample was stored in a closed container for preventing vaporization of light materials to minimize occurrence of a gas phase.
  (2) Flash point: A sample was obtained from the stream of the sample to be measured and measurement was performed based on ASTM D93 using apm-8 available from TANAKA. In addition, the temperature of each of the samples was maintained at a temperature lower than an expected flash point by 10° C., and the sample was stored in a closed container for preventing vaporization of light materials to minimize occurrence of a gas phase.

Comparative Examples

Comparative Example 1

According to the process flow diagram illustrated in FIG. 2, synthesis gas was prepared.

Specifically, the lower discharge stream discharged at the stage of 100% of the total number of stages of the gasoline fractionator 10 in the naphtha cracking center process (S1) was supplied to the second stripper 30, and the pyrolysis fuel oil (PFO) stream containing PFO was discharged from the lower portion of the second stripper 30.

The PFO stream was supplied to the combustion chamber in the gasification process (S3) together with oxygen and vapor. At this time, it was confirmed that the content of C13+ in the PFO stream was 89 wt %, and the PFO stream had a flash point of 98° C. and a kinematic viscosity at 40° C. of 660 cSt.

In addition, the upper discharge stream discharged at the stage of 1% of the total number of stages of the gasoline fractionator 10 in the naphtha cracking center process (S1) was supplied to the NCC subsequent process (not illustrated), and an RPG stream containing styrene and an RPG stream containing no styrene were discharged in the NCC subsequent process.

The RPG stream containing styrene was supplied to the SM process unit in the SM/BTX preparation process (S4) to prepare styrene using the C7 separation column, the C8 separation column, and the extractive distillation column, and the residual stream from the SM process unit was supplied to the BTX process unit.

The RPG stream containing no styrene and the residual stream from the SM process unit were supplied to the BTX process unit in the SM/BTX preparation process (S4) to prepare benzene, toluene, and xylene using the hydrodesulfurization unit, the C5 separation column, the C7 separation column, the extractive distillation column, the benzene separation column, the toluene separation column, and the xylene separation column.

The temperature of the PFO stream at the time of supply to the combustion chamber was measured. The result is shown in Table 2. In addition, it was confirmed whether the process operating standards were satisfied according to the measurement results. At this time, the time when the PFO stream was supplied to the combustion chamber was set to temperature conditions to control the kinematic viscosity to 300 cSt using the heat exchanger.

In addition, the production of styrene, benzene, toluene, and xylene produced in the SM/BTX preparation process (S4) is shown in Table 3.

Comparative Example 2

According to the process flow diagram illustrated in FIG. 3, synthesis gas was prepared.

Specifically, the side discharge stream discharged at the stage of 40% of the total number of stages of the gasoline fractionator 10 in the naphtha cracking center process (S1) was supplied to the first stripper 20, and the pyrolysis gas oil (PGO) stream containing PGO was discharged from the lower portion of the first stripper 20.

The PGO stream was supplied to the combustion chamber in the gasification process (S3) together with oxygen and vapor. At this time, it was confirmed that the content of C10 to C12 in the PGO stream was 86 wt %, and the PGO stream had a flash point of 25.5° C. and a kinematic viscosity at 40° C. of 75 cSt.

In addition, the upper discharge stream discharged at the stage of 1% of the total number of stages of the gasoline fractionator 10 in the naphtha cracking center process (S1) was supplied to the NCC subsequent process (not illustrated), and an RPG stream containing styrene and an RPG stream containing no styrene were discharged in the NCC subsequent process.

The RPG stream containing styrene was supplied to the SM process unit in the SM/BTX preparation process (S4) to prepare styrene using the C7 separation column, the C8 separation column, and the extractive distillation column, and the residual stream from the SM process unit was supplied to the BTX process unit.

The RPG stream containing no styrene and the residual stream from the SM process unit were supplied to the BTX process unit in the SM/BTX preparation process (S4) to prepare benzene, toluene, and xylene using the hydrodesulfurization unit, the C5 separation column, the C7 separation column, the extractive distillation column, the benzene separation column, the toluene separation column, and the xylene separation column.

The temperature of the PGO stream at the time when the PGO stream was supplied to the combustion chamber was measured. The result is shown in Table 2. In addition, it was confirmed whether the process operating standards were satisfied according to the measurement results. At this time, the time when the PGO stream was supplied to the combustion chamber was set to temperature conditions to control the kinematic viscosity to 300 cSt using the heat exchanger.

In addition, the production of styrene, benzene, toluene, and xylene produced in the SM/BTX preparation process (S4) is shown in Table 3.

Comparative Example 3

According to the process flow diagram illustrated in FIG. 4, synthesis gas was prepared.

Specifically, the side discharge stream discharged at the stage of 40% of the total number of stages of the gasoline fractionator 10 in the naphtha cracking center process (S1) was supplied to the first stripper 20, and then the pyrolysis gas oil (PGO) stream containing PGO was discharged from the lower portion of the first stripper 20, and at this time, it was confirmed that a content of C10 to C12 in the PGO stream was 86 wt %. In addition, the lower discharge stream discharged at the stage of 100% of the total number of stages of the gasoline fractionator 10 was supplied to the second stripper 30, and then the pyrolysis fuel oil (PFO) stream containing PFO was discharged from the lower portion of the second stripper 30, and at this time, it was confirmed that a content of C13+ in the PFO stream was 89 wt %.

Next, a mixed oil stream was produced by mixing the PGO stream and the PFO stream. At this time, the PGO stream had a flash point of 25.5° C. and a kinematic viscosity at 40° C. of 75 cSt, and the PFO stream had a flash point of 98° C. and a kinematic viscosity at 40° C. of 660 cSt. In addition, a ratio of a flow rate of the PGO stream to a flow rate of the mixed oil stream was 0.42. Then, the mixed oil stream was supplied to the combustion chamber in the gasification process (S3) together with oxygen and vapor.

In addition, the upper discharge stream discharged at the stage of 1% of the total number of stages of the gasoline fractionator 10 in the naphtha cracking center process (S1) was supplied to the NCC subsequent process (not illustrated), and an RPG stream containing styrene and an RPG stream containing no styrene were discharged in the NCC subsequent process.

The RPG stream containing styrene was supplied to the SM process unit in the SM/BTX preparation process (S4) to prepare styrene using the C7 separation column, the C8 separation column, and the extractive distillation column, and the residual stream from the SM process unit was supplied to the BTX process unit.

The RPG stream containing no styrene and the residual stream from the SM process unit were supplied to the BTX process unit in the SM/BTX preparation process (S4) to prepare benzene, toluene, and xylene using the hydrodesulfurization unit, the C5 separation column, the C7 separation column, the extractive distillation column, the benzene separation column, the toluene separation column, and the xylene separation column.

The flash point of the mixed oil stream and the temperature when the mixed oil stream was supplied to the combustion chamber were measured. The results are shown in Table 2. In addition, it was confirmed whether the process operating standards were satisfied according to the measurement results. At this time, the time when the mixed oil stream was supplied to the combustion chamber was set to temperature conditions to control the kinematic viscosity to 300 cSt using the heat exchanger.

In addition, the production of styrene, benzene, toluene, and xylene produced in the SM/BTX preparation process (S4) is shown in Table 3.

Comparative Example 4

Styrene and BTX were prepared in the same manner as that of Example 1, except that the upper discharge stream from the distillation tower 50 was not supplied to the SM/BTX preparation process (S4) in Example 1.

In addition, the production of styrene, benzene, toluene, and xylene produced in the SM/BTX preparation process (S4) is shown in Table 3.

TABLE 1

| | | Ratio of C6 to C8 aromatic hydrocarbons | | Temperature of lower discharge | Kinematic viscosity of lower discharge | Flash point | Whether process |
|---|---|---|---|---|---|---|---|
| | Distillation ratio | Upper discharge stream | Lower discharge stream | stream at time of supply (° C.) | stream at time of supply (cSt) | of lower discharge stream (° C.) | operating standards are satisfied |
| Example 1 | 0.005 | 0 | 1 | 48.3 | 300 | 73 | X |
| Example 2 | 0.01 | 0.08 | 0.92 | 49.2 | 300 | 75 | ○ |
| Example 3 | 0.1 | 1 | 0 | 60 | 300 | 90.5 | ○ |
| Example 4 | 0.2 | 1 | 0 | 73.3 | 300 | 99 | ○ |
| Example 5 | 0.3 | 1 | 0 | 97.6 | 300 | 105.5 | X |

TABLE 2

| | Flash point of stream (° C.) | Kinematic viscosity of stream at time of supply (cSt) | Temperature of stream at time of supply (° C.) | Whether process operating standards are satisfied |
|---|---|---|---|---|
| Comparative Example 1 (PFO) | 98 | 300 | 78 | X |
| Comparative Example 2 (PGO) | 25.5 | 300 | 14 | X |
| Comparative Example 3 (Mixed oil) | 70 | 300 | 47 | X |

TABLE 3

| | Production of benzene (%) | Production of toluene (%) | Production of xylene (%) | Production of styrene (%) |
|---|---|---|---|---|
| Example 1 | 100.0 | 100.0 | 100.0 | 100.0 |
| Example 2 | 100.1 | 100.1 | 100.0 | 100.0 |
| Example 3 | 100.2 | 100.8 | 107.0 | 111.0 |
| Example 4 | 100.2 | 100.8 | 107.0 | 111.0 |
| Example 5 | 100.2 | 100.8 | 107.0 | 111.0 |
| Comparative Example 1 | 100.0 | 100.0 | 100.0 | 100.0 |
| Comparative Example 2 | 100.0 | 100.0 | 100.0 | 100.0 |
| Comparative Example 3 | 100.0 | 100.0 | 100.0 | 100.0 |
| Comparative Example 4 | 100.0 | 100.0 | 100.0 | 100.0 |

In Tables 1 and 2, whether the process operating standards were satisfied was indicated by 0 when the temperature at the time when the stream supplied to the combustion chamber in each of Examples 1 to 5 and Comparative Examples 1 to 3 was supplied to the combustion chamber at which the kinematic viscosity at the time of supply to the combustion chamber was 300 cSt was lower than the flash point by 25° C. or more, and was indicated by X when the temperature did not satisfy the above-described condition.

In addition, in Table 3, the production of each of benzene, toluene, xylene, and styrene was expressed as a relative production ratio of each of benzene, toluene, xylene, and styrene calculated based on the production (100%) of each of benzene, toluene, xylene, and styrene in Comparative Example 1.

Referring to Tables 1 and 2, in Examples 2 to 4 in which according to the method for preparing synthesis gas of the present invention, the distillation ratio of the distillation tower 50 was adjusted to the appropriate range (0.01 to 0.2) to produce the lower discharge stream, and the lower discharge stream from the distillation tower 50 was supplied to the combustion chamber for the gasification process (S3), it could be confirmed that when the lower discharge stream from the distillation tower 50 was supplied to the combustion chamber, the flash point of the lower discharge stream from the distillation tower 50 was higher than the temperature of the lower discharge stream from the distillation tower 50 at the time of supply to the combustion chamber by 25° C. or more, and the kinematic viscosity thereof was in a range of 300 cSt or less at the temperature of the lower discharge stream from the distillation tower 50 at the time of supply to the combustion chamber. It was confirmed that since both the flash point and the kinematic viscosity were in the ranges as such, the process operating conditions for use as the raw material for the gasification process (S3) were satisfied.

In particular, as illustrated in FIG. 1, in Example 3 in which the distillation ratio of the distillation tower 50 in the pretreatment process (S2) was controlled to a range of 0.03 to 0.15, it was confirmed that when the lower discharge stream from the distillation tower 50 was supplied to the combustion chamber, the flash point of the lower discharge stream from the distillation tower 50 was higher than the temperature of the lower discharge stream from the distillation tower 50 at the time of supply to the combustion chamber by 30° C. or more to allow more stable operation.

In addition, in Examples 1 to 5 in which the lower discharge stream to be discharged from the distillation tower 50 was formed in the state where the distillation ratio of the distillation tower 50 was not adjusted to the appropriate range (0.01 to 0.2), it was appreciated that when the kinematic viscosity at the temperature of the lower discharge stream from the distillation tower 50 at the time of supply to the combustion chamber was controlled to 300 cSt, the temperature of the lower discharge stream from the distillation tower 50 at the time of supply to the combustion chamber was not controlled to be lower than the flash point by 25° C. or more.

On the other hand, when the PFO stream was directly supplied to the combustion chamber without the pretreatment process (S2) as illustrated in FIG. 2 (Comparative Example 1), the PGO stream was directly supplied to the combustion chamber without the pretreatment process (S2) as illustrated in FIG. 3 (Comparative Example 2), or the mixed oil stream of the PGO stream and the PFO stream was directly supplied to the combustion chamber without the pretreatment process (S2) according to the present invention as illustrated in FIG. 4 (Comparative Example 3), it could be confirmed that a temperature satisfying both the kinematic viscosity and the flash point in the appropriate ranges described above did not exist. As such, it was confirmed that each of the streams of Comparative Examples 1 to 3 which did not satisfy both the kinematic viscosity and the flash point in the appropriate ranges did not satisfy the process operating conditions for use as the raw material for the gasification process (S3).

When the raw material for the gasification process (S3) is supplied to the combustion chamber at the temperature which does not satisfy any one of the kinematic viscosity and the flash point in the appropriate ranges, a differential pressure in the combustion chamber may be raised or atomization may not be smoothly performed to deteriorate combustion performance, and an explosion risk may be increased due to excessive oxygen, or a flame may occur in the burner before combustion reaction occurrence, and an explosion risk may be present due to a backfire phenomenon of the flame in the combustion chamber and refractories in the combustion chamber may be damaged.

In addition, referring to Table 3, it can be confirmed that in Examples 1 to 5, the production of benzene, toluene, xylene, or styrene in the SM/BTX preparation process (S4) varies depending on the distillation ratio of the distillation tower 50, and the production is increased compared to Comparative Examples. Specifically, it could be confirmed that when the distillation ratio of the distillation tower 50 was controlled to 0.01 or more, the C6 to C8 aromatic hydrocarbons were discharged through the upper discharge stream of the distillation tower 50, and in particular, when the distillation ratio of the distillation tower 50 was 0.1 or more, the entire amount of the C6 to C8 aromatic hydrocarbons was discharged through the upper portion of the distillation tower 50. Therefore, it could be confirmed that controlling the distillation ratio of the distillation tower 50 to 0.1 to 0.2 was the optimal process condition for preparing styrene and BTX together with synthesis gas.

The invention claimed is:

1. A method for preparing synthesis gas and aromatic hydrocarbons, the method comprising:
   supplying a pyrolysis fuel oil (PFO) stream containing PFO and a pyrolysis gas oil (PGO) stream containing PGO to a distillation tower as a feed stream (S10), the PFO stream and the PGO stream being discharged from a naphtha cracking center (NCC) process; and
   supplying a lower discharge stream from the distillation tower to a combustion chamber for a gasification process to obtain synthesis gas and supplying an upper discharge stream from the distillation tower to a preparation process (SM/BTX preparation process) including a preparation process of styrene (SM preparation process) and a preparation process of one or more of benzene, toluene, and xylene (BTX preparation process) to obtain aromatic hydrocarbons (S20),
wherein a ratio of a flow rate of the upper discharge stream from the distillation tower to a flow rate of the feed stream to be supplied to the distillation tower is 0.01 to 0.2, and
wherein a kinematic viscosity of the lower discharge stream from the distillation tower at the time of supply to the combustion chamber is controlled to have 300 cSt or less.

2. The method of claim 1, wherein the ratio of the flow rate of the upper discharge stream from the distillation tower to the flow rate of the feed stream to be supplied to the distillation tower is 0.1 to 0.2.

3. The method of claim 1,
wherein a flash point of the lower discharge stream from the distillation tower is higher than a temperature of the lower discharge stream at the time of supply to the combustion chamber by 25° C. or more.

4. The method of claim 1, wherein a temperature of the lower discharge stream from the distillation tower at the time of supply to the combustion chamber is 20° C. to 90° C.

5. The method of claim 1, wherein the lower discharge stream from the distillation tower passes through a heat exchanger before being supplied to the combustion chamber.

6. The method of claim 1, wherein the PGO stream contains 70 wt % or more of hydrocarbons having 10-12 carbon atoms, and
wherein the PFO stream contains 70 wt % or more of hydrocarbons having 13 or more carbon atoms.

7. The method of claim 1, wherein a flash point of the PGO stream is 10 to 50° C., and
wherein a flash point of the PFO stream is 70 to 200° C.

8. The method of claim 1, wherein a kinematic viscosity of the PGO stream at 40° C. is 1 to 200 cSt, and
wherein a kinematic viscosity of the PFO stream at 40° C. is 400 to 100,000 cSt.

9. The method of claim 1, wherein a raw pyrolysis gasoline (RPG) stream containing RPG discharged from the naphtha cracking center (NCC) process is supplied to the SM/BTX preparation process.

10. The method of claim 1, wherein the PGO stream is a lower discharge stream discharged from a lower portion of a first stripper after supplying a side discharge stream discharged from a side portion of a gasoline fractionator in the naphtha cracking center (NCC) process to the first stripper, and
wherein the PFO stream is a lower discharge stream discharged from a lower portion of a second stripper after supplying a lower discharge stream discharged from a lower portion of the gasoline fractionator in the naphtha cracking center (NCC) process to the second stripper.

11. The method of claim 10, wherein the lower discharge stream from the gasoline fractionator is discharged at a stage of 90% or more of a total number of stages of the gasoline fractionator, and
wherein the side discharge stream from the gasoline fractionator is discharged at a stage of 10% to 70% of the total number of stages of the gasoline fractionator.

12. The method of claim 1, wherein a reflux ratio of the distillation tower is 0.01 to 10.

13. The method of claim 1, wherein the SM/BTM preparation process includes an SM process unit and a BTX process unit, and the upper discharge stream from the distillation tower is supplied to the SM process unit in the SM/BTX preparation process.

* * * * *